(12) United States Patent
Hatanaka et al.

(10) Patent No.: US 7,222,515 B2
(45) Date of Patent: May 29, 2007

(54) IMPACT TEST APPARATUS AND IMPACT TEST METHOD

(75) Inventors: Takezou Hatanaka, Ibaraki (JP); Yasunori Sugihara, Ibaraki (JP); Junji Yoshida, Ibaraki (JP); Yukiko Azumi, Ibaraki (JP); Yuuki Kagehisa, Ibaraki (JP)

(73) Assignee: Nitto Denki Corporation, Osaka (JP)

( * ) Notice: Subject to any disclaimer, the term of this patent is extended or adjusted under 35 U.S.C. 154(b) by 49 days.

(21) Appl. No.: 11/143,502

(22) Filed: Jun. 3, 2005

(65) Prior Publication Data

US 2006/0005606 A1    Jan. 12, 2006

(30) Foreign Application Priority Data

Jul. 8, 2004    (JP) .............................. 2004-202435
Mar. 15, 2005   (JP) .............................. 2005-072186

(51) Int. Cl.
*G01M 3/00* (2006.01)
*G01N 33/00* (2006.01)

(52) U.S. Cl. ................. 73/12.14; 73/12.01; 73/12.09
(58) Field of Classification Search ............... 73/12.14, 73/12.09
See application file for complete search history.

(56) References Cited

U.S. PATENT DOCUMENTS

| 2,450,880 | A | * | 10/1948 | Chatten et al. ............ 73/12.14 |
| 2,766,624 | A | * | 10/1956 | Heffner ..................... 73/865.6 |
| 3,289,470 | A | | 12/1966 | Hubin |
| 3,333,461 | A | * | 8/1967 | Gordon et al. ................ 73/769 |
| 3,693,421 | A | * | 9/1972 | Karper et al. .................. 73/843 |
| 4,405,243 | A | | 9/1983 | Kuraoka et al. |
| 4,649,735 | A | * | 3/1987 | Pihlaja ....................... 73/12.13 |
| 5,770,791 | A | | 6/1998 | Manahan, Sr. |
| 5,789,681 | A | * | 8/1998 | Angley et al. ................. 73/803 |
| 6,202,496 | B1 | * | 3/2001 | Jakob et al. ................... 73/866 |
| 6,324,915 | B1 | | 12/2001 | Potts |
| 2003/0003857 | A1 | * | 1/2003 | Shimagaki et al. ......... 451/534 |
| 2004/0040369 | A1 | | 3/2004 | Hoo Fatt et al. |

FOREIGN PATENT DOCUMENTS

| GB | 513319 | 10/1939 |
| GB | 1172538 | 12/1969 |
| JP | A 02-013825 | 1/1990 |

OTHER PUBLICATIONS (A. J. Kalkman and A. H. Verbruggen. High-temperature bulge-test setup for mechanical testing of free-standing thin films. Rev. Sci. Instrum. 74, 1383 (2003) accessed online: Sep. 18, 2006. http://scitation.aip.org).*

"Testing Methods of Rebound Resilience For Rubber, Vulcanized or Thermoplastic"; Japanese Standards Association JIS Handbook Rubber; pp. 307-317; 1996.

* cited by examiner

*Primary Examiner*—Edward Lefkowitz
*Assistant Examiner*—Punam Patel
(74) *Attorney, Agent, or Firm*—Oliff & Berridge, PLC (57) ABSTRACT

An impact test apparatus includes a holding device for holding a test piece at an arbitrary holding force, an impact applying device for applying an impact force to the test piece held by the holding device, a force sensor for sensing the impact force applied to the test piece by the impact applying device, a high-speed camera for detecting a displacement of the test piece when applied with the impact force by the impact applying device, and an output device for synchronizing a signal from the force sensor with a signal from the high-speed camera and outputting an impact stress-strain characteristic curve when the impact force is applied to the test piece.

14 Claims, 9 Drawing Sheets

IMPACT TEST APPARATUS AND IMPACT TEST METHOD

BACKGROUND OF THE INVENTION

1. Field of the Invention

The present invention relates to an impact test apparatus and an impact test method that can obtain an impact stress-strain characteristic of a test piece.

2. Description of Related Art

An Izod impact test or a Charpy impact test has been conventionally known as a method of measuring the impact strength of a material (for example, see Japanese Unexamined Patent Publication No. H2(1990)-13825). According to these methods, when an impact energy (impact force) is applied to a test piece to break a test piece, the impact strength of the test piece can be measured from the impact energy. However, in the case of a test piece formed of an impact absorbing material of a foaming material, a viscoelastic material, or a combination of these materials, when the impact force is applied to the test piece, the test piece is elastically deformed to absorb the impact energy (impact force). Hence, it is difficult to evaluate an impact force applied to the test piece and an impact stress-strain characteristic of the test piece when the impact force is applied to the test piece. For this reason, in the impact absorbing material, the characteristic of the impact absorbing material has been evaluated by measuring an impact absorbing property or an repulsion property that are found by a Lubke impact resilience test method or a Trypso impact resilience test method (see, for example, Japanese Standards Association JIS Handbook Rubber (issued on Apr. 1, 1999).

By the way, a foaming material, a viscoelastic material, or a combination of these materials has been used as the impact absorbing material of various kinds of machines and electric appliances. Portable machines and electric appliances (for example, cellular mobile phone) have been increased in number in recent years. In these various products, an impact force is applied to them in a manner that has never been hitherto conceivable.

Moreover, these impact absorbing materials have different impact absorbing properties according to material, internal form, or the like. Hence, it becomes difficult to evaluate the impact absorbing materials by the conventional impact tests or repulsion elasticity test on the same basis. Therefore, these impact absorbing materials are placed on actual products and impact drop tests or the like are conducted on the actual products. In this manner, a durability evaluation test or the like for impact is conducted on the product.

SUMAMRY OF THE INVENTION

However, as product diversification has been increased and product development has been accelerated in recent years, for the purpose of controlling the quality of an impact absorbing material without conducting an impact test on an actual product, a method of evaluating an impact absorbing material has been demanded by which an impact force is applied to a test piece formed of the impact absorbing material to obtain an impact stress-strain characteristic and the like.

The present invention has been made to solve the above demand. The object of the invention is to provide an impact test apparatus and an impact test method that can obtain an impact stress-strain characteristic and the like when an impact force is applied to an impact absorbing material including a foaming material, a viscoelastic material, or a combination of these materials.

To achieve the above purpose of the invention, there is provided an impact test apparatus comprising: a holding device for holding a test piece at an arbitrary holding force; an impact applying device for applying an impact force to the test piece held by the holding device; an impact force sensing device for sensing the impact force applied to the test piece by the impact applying device; a displacement detecting device for detecting a displacement of the test piece when the impact force sensing device senses the impact force; and an output device for outputting impact stress-strain characteristic information expressing a relationship between an impact stress and a strain corresponding to the impact stress of the test piece on the basis of the impact force sensed by the impact force sensing device and the displacement detected by the displacement detecting device.

With the above structure, the impact test apparatus can hold a test piece at an arbitrary holding force and apply an impact force to the test piece. Moreover, impact stress-strain characteristic information expressing the relationship between an impact stress and a strain to the impact stress of the test piece can be obtained on the basis of the impact force, which is applied to the test piece and is sensed by an impact force sensing device, and the displacement of the test piece, which is detected by a displacement detecting device when the impact force is applied to the test piece.

According to another aspect of the invention, there is provided an impact test method comprising the steps of: holding a test piece at an arbitrary holding force by a holding device; applying an impact force to the test piece held at the holding step by an impact applying device; sensing the impact force applied to the test piece at the impact applying step by an impact force sensing device and of detecting a displacement of the test piece when the impact force sensing device senses the impact force by a displacement detecting device; and outputting impact stress-strain characteristic information expressing a relationship between an impact stress and a strain corresponding to the impact stress of the test piece on the basis of the impact force and the displacement, which are sensed and detected at the detecting step, by an output device.

In the above-described impact test method, at a holding step, a test piece is held at an arbitrary holding force, and at an impact applying step an impact force can be applied to the test piece. Moreover, at a detecting step, the impact force applied to the test piece is sensed and the displacement of the test piece when the impact force is sensed is detected. Then, at an output step, impact stress-strain characteristic information expressing the relationship between an impact stress and a strain to the impact stress of the test piece can be obtained on the basis of the sensed impact force and the detected displacement.

Further, according to another aspect of the invention, there is provided an impact test method comprising the steps of: applying an impact force by an impact applying device in a state where a test piece is not set in a holding device; sensing the impact force at the first impact applying step by an impact force sensing device; holding the test piece at an arbitrary force by the holding device; applying an impact force to the test piece held at the holding step by the impact applying device; sensing the impact force applied to the test piece at the second impact applying step by the impact force sensing device; and outputting an impact absorption rate of the test piece by dividing an impact force, which is found by subtracting the impact force sensed at the second sensing step from the impact force sensed at the first sensing step, by the impact force sensed at the first sensing step to find an impact absorption rate.

In the above-described impact test method, first, at the first sensing step, an impact force is sensed which is applied by the impact applying device in a state where a test piece is not set in a holding device; next, a test piece is held at an arbitrary holding force by the holding device, and then at the second sensing step an impact force applied to the test piece by the impact force applying device is sensed. Then, an impact force, which is obtained by subtracting the impact force sensed at the second sensing step from the impact force sensed at the first sensing step, is divided by the impact force sensed at the first sensing step, whereby the impact absorption rate of the test piece can be obtained.

DETAILED DESCRIPTION OF THE PREFERRED EMBODIMENTS

Hereafter, a first and a second embodiments in which an impact test apparatus and an impact test method in accordance with the present invention are embodied will be described with reference to the drawings.

Embodiment 1

First, the schematic construction of an impact test apparatus in a first will be described with reference to FIGS. 1 to 4.

As shown in FIGS. 1 to 4, an impact test apparatus 1 in the first embodiment is constructed of: a holding device 3 for holding a test piece 2 at an arbitrary force; an impact applying device 4 for applying an impact stress to the test piece 2; a force sensor 5 as an impact force sensing device for sensing an impact force applied to the test piece 2 by the impact applying device 4; a high-speed camera 6 as a displacement detecting device for detecting the displacement of the test piece when the impact applying device 4 applies an impact force to the test piece 2; and an output device 7 for synchronizing a signal from the force sensor 5 with a signal from the high-speed camera 6 and outputting an impact stress-strain characteristic curve as impact stress-strain characteristic information expressing the relationship between an impact stress of the test piece and a strain to the impact stress when an impact force is applied to the test piece 2.

Further, the holding device 3 for holding the test piece 2 at an arbitrary holding force is constructed of a fixing jig 11 fixed to a table 10 and a pressing member 12 that is opposed to the fixing jig 11 to sandwich the test piece 2 between them and can slide so as to be able to hold the test piece 2. The pressing member 12 is slidably placed on a base 13 sliding on the table 10 and can slide on the table 10 along with the base 13. Further, the base 13 is provided with a lever 14 for sliding the base 13 and a fixing member 15 for fixing the base 13 to the table 10 after the base 13 is slid by the lever 14 and is temporarily positioned. Still further, the pressing member 12 is provided with a pressing pressure adjusting unit 16. The pressing pressure adjusting unit 16 is preferably provided with a digital gage or the like moving in response to the pressing member 12. The pressing pressure adjusting unit 16 can finely adjust the pressing member 12 on the base 13 fixed at a temporary position in the back-and-forth direction (in the left-and-right direction in FIG. 1) with respect to the test piece 2, thereby being able to adjust a holding force applied to the held test piece 2.

Figure 1:
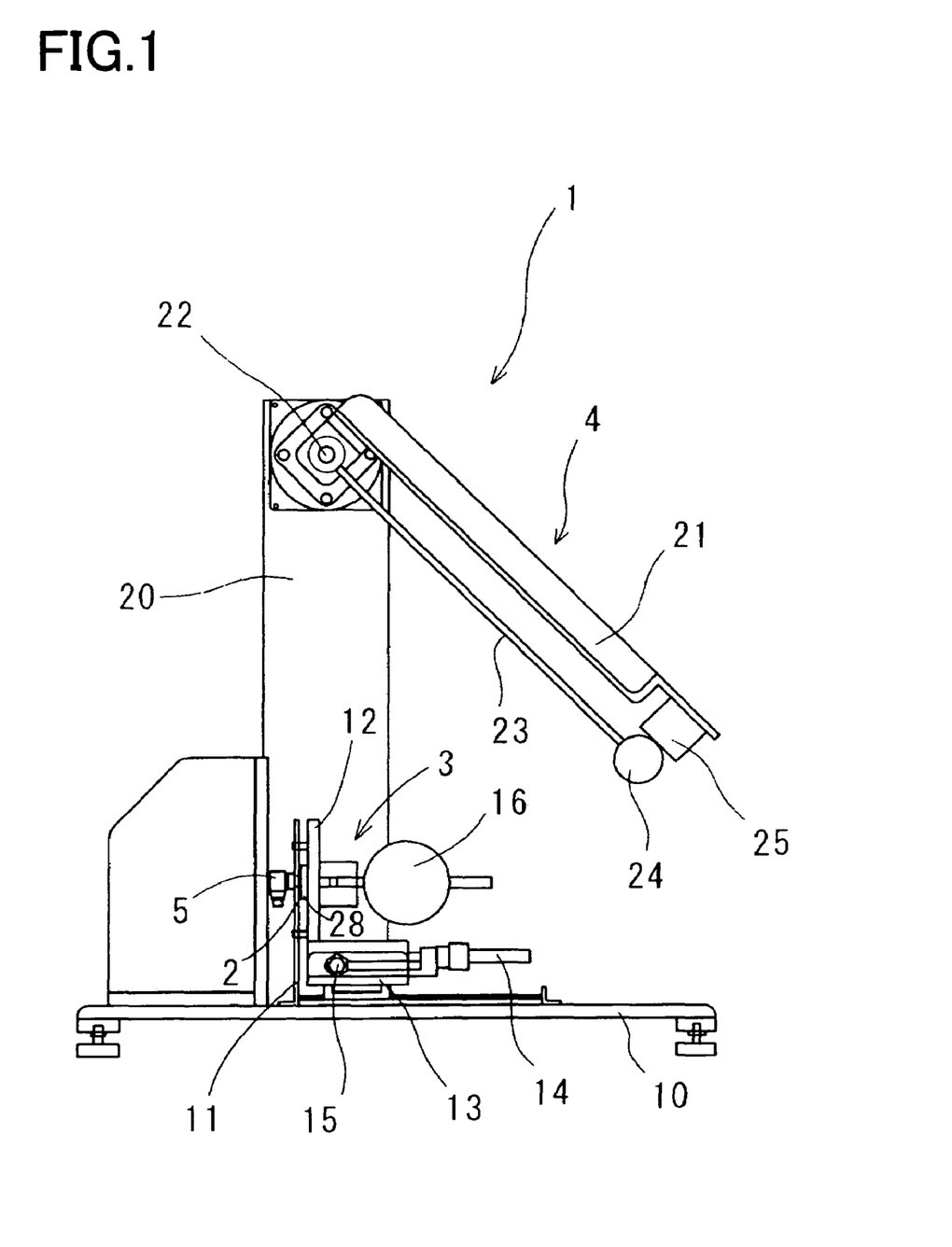
FIG. 1 is a front view showing a schematic construction of an impact test apparatus in a first embodiment.
Figure 2:
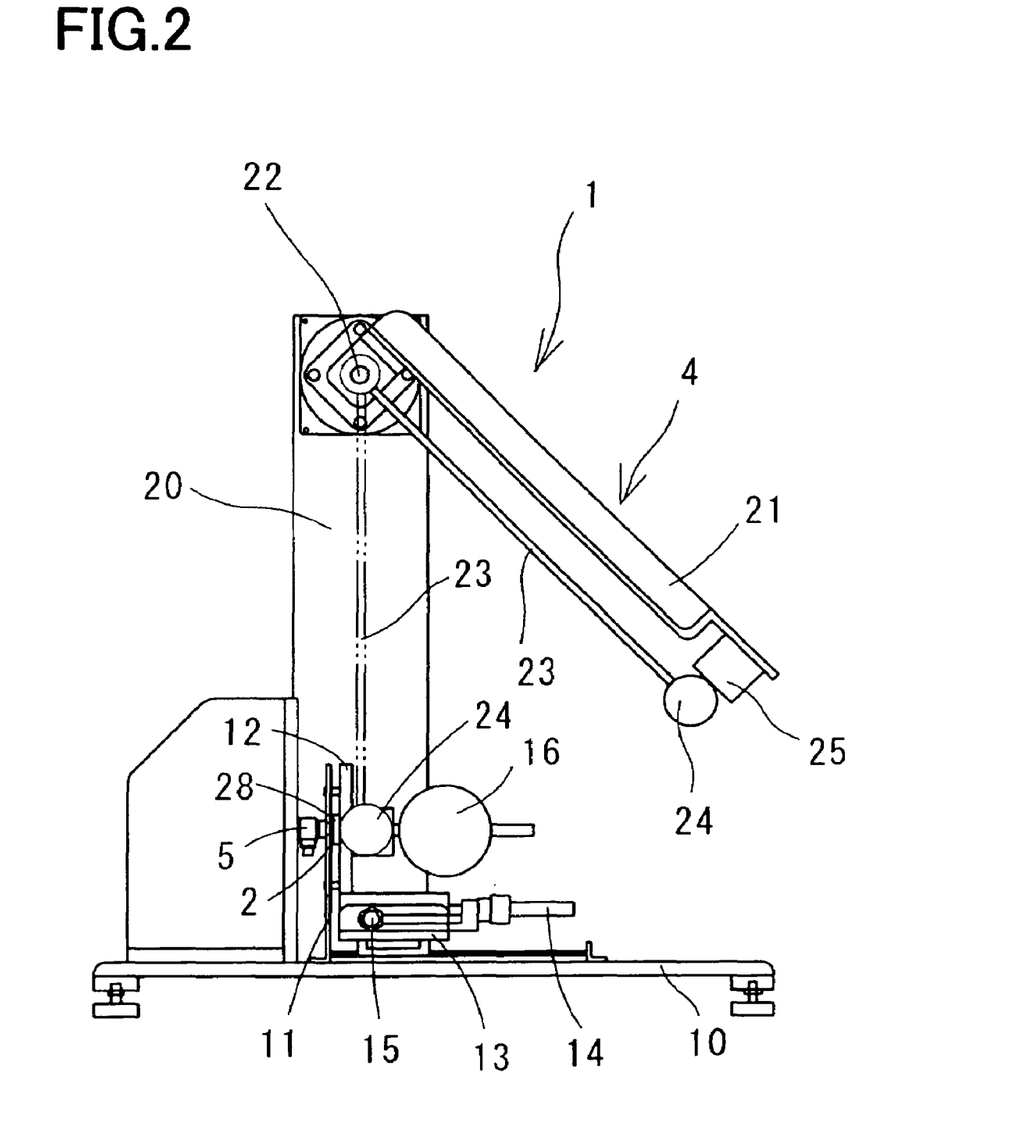
FIG. 2 is a front view illustrating a state where an impact force is applied to a test piece in the impact test apparatus in the first embodiment.
Figure 3A:
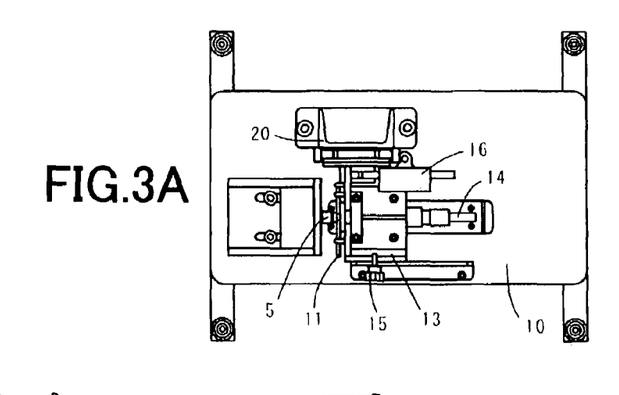
FIGS. 3A to 3D are a plan view, a front view, a left side view, and a right side view showing the schematic construction of the impact test apparatus in the first embodiment.
Figure 3B:
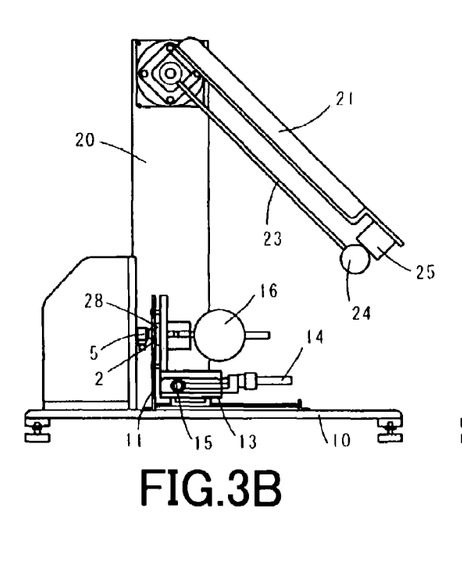
Figure 3C:
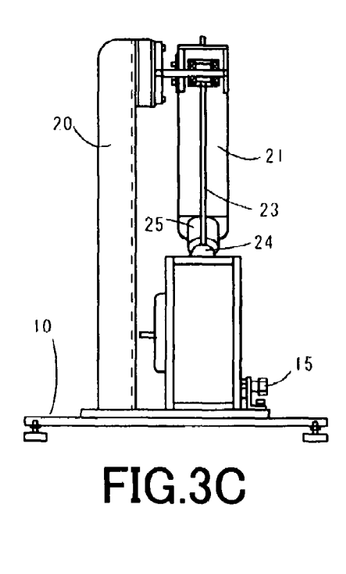
Figure 3D:
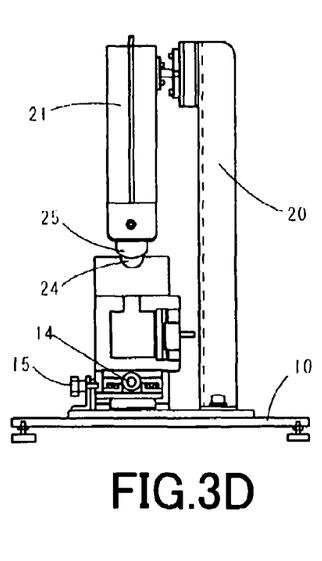

Further, an impact applying device 4 for applying an impact force to the test piece 2 held by the holding device 3 is constructed of a shaft 23 having one end 22 that is turnably journaled by a support column 20 and a hammer 24 at the other end, and an arm 21 that lifts the hammer 24 to a predetermined angle and holds it. The arm 21 can be fixed and held at the predetermined angle. Here, the hammer 24 is made of a steel ball and can be lifted to the predetermined angle along with the arm 21 by an electric magnet 25 fixed to one end of the arm 21. In this regard, the electric magnet 25 is used here but any other part can be used which can lift the hammer 24 along with the arm 21 and can easily separate the hammer from the arm 21. Moreover, the hammer 24 is not limited to a ball but may be, for example, a block.

Still further, the force sensor 5 for sensing an impact force applied to the test piece by the impact applying device 4 is fixed to such a surface of the fixing jig 11 that is opposite to a surface in contact with the test piece 2. A force sensor constructed of a piezoelectric device is preferably used as the force sensor 5 in the first embodiment. When the hammer 24 of the impact applying device 4 applies an impact force to the test piece 2, the force sensor 5 can sense the impact force with reliability. Here, in place of the force sensor 5, a strain gage can be also employed.

Figure 4:
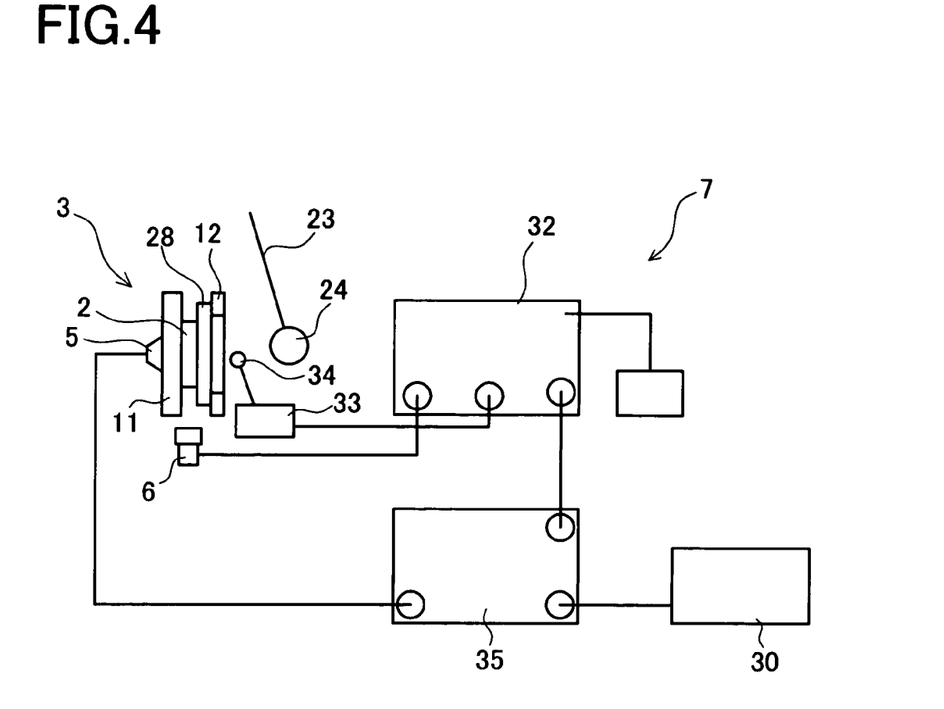
FIG. 4 shows the schematic construction of an output device that detects the impact force and displacement of a test piece and outputs impact stress-strain characteristic information in the impact test apparatus in the first embodiment.

Still further, the high-speed camera 6 for detecting the displacement of the test piece 2 when the impact force is applied to the test piece 2, as shown in FIG. 4, a high-speed camera capable of directly observing the displacement of the test piece 2 is preferably used. Here, it is preferable that the high-speed camera can take pictures at intervals of 200 μsec or less, more preferably, at intervals of 100 μsec or less, and still more preferably, at intervals of 75 μsec or less.

Still further, as shown in FIG. 4, the test piece 2 is sandwiched between the fixing jig 11 and the pressing member 12 via a supporting plate 28 constructed of a highly elastic plate such as a resin plate made of acrylic resin or the like or a metal plate made of aluminum or the like.

Still further, as shown in FIG. 4, the output device 7 for outputting an impact stress-strain characteristic curve is constructed of: the first control section 32 for outputting a displacement detecting signal (image signal) from the high-speed camera 6 serving as the displacement detecting device; synchronizing section 35 for synchronizing a signal from the force sensor 5 serving as the impact force sensing device with a displacement detecting signal (image signal) from the first control section 32; and the second control section 30 that analyzes an image of the displacement detecting signal (image signal) from the first control section 32, divides a displacement by the thickness of the test piece 2 when load is not applied thereto to calculate a strain, analyzes a signal from the force sensor 5 synchronized by the synchronizing section 35 and calculates an impact force, divides the impact force by the area of such surface of the test piece 2 that abuts against the supporting plate 28 to calculate an impact stress, and outputs an impact stress-strain characteristic curve. Here, the synchronization between the signal from the force sensor 5 and the displacement detecting signal (image signal) from the first control section 32 is achieved by the simultaneous detection of the respective signals by the first control section 32 and the synchronizing section 35 at a timing of a signal from a speed meter 33 outputted when the hammer 24 passes before a speed sensor 34 disposed before the test piece 2.

Next, an impact test method using the impact test apparatus 1 constructed in the manner described above will be described.

(Holding Step)

First, the test piece 2 is not inserted between the fixing jig 11 and the pressing member 12 of the holding device 3 but only the supporting plate 28 made of acrylic resin is inserted. Then, the base 13 is slid to the fixing jig 11 side by the lever 14, thereby being into nearly close contact with the supporting plate 28 and then being temporarily fixed there. Next, the base 13 is finely adjusted by the pressing pressure adjusting unit 16 to put the fixing jig 11 into close contact with the supporting plate 28. At this time, a memory provided in the pressing pressure adjusting unit 16 is reset and the position of the pressing member 12 is made a base point.

Next, the thickness of the test piece 2 is previously measured. The pressing pressure adjusting unit 16 is adjusted to move the pressing member 12 from the base point by the thickness of the test piece 2 to set the test piece 2 between the fixing jig 11 and the supporting plate 28. At this time, in the case of setting the test piece 2 made of an impact absorbing material, which is made of a foaming material, a viscoelastic material, or a combination of these materials and damps and absorbs an impact force when the impact force is applied to the test piece 2, in the holding device 3, a pressing pressure is adjusted while checking the gage of the pressing pressure adjusting unit 16 and considering the thickness of the test piece 2. In this manner, the test piece 2 can be fixed at a compression rate close to a compression rate in the actual state of placement of a product. Further, when an adhesive agent or the like is applied to a portion or the whole of one surface of the test piece 2, the test piece 2 can be placed on the fixing jig 11 and hence can be fixed to the fixing jig 11 with reliability.

(Impact Applying Step)

After the test piece 2 is set, the switch of the electric magnet 25 fixed to one end of the arm 21 is turned on to fixedly hold the hammer 24 by the arm 21. The arm 21 is swung up to an arbitrary angle and is fixed there and then the switch of the electric magnet 25 is turned off to bring the hammer 24 into collision with the supporting plate 28 held by the holding device 3 (see FIG. 2).

(Detecting Step)

Moreover, an impact force at this time is measured by the force sensor 5. Here, the fixing jig 11 is put into close contact with the supporting plate 28 before the test piece 2 is inserted between them and then the hammer 24 is similarly brought into collision with the supporting plate 28 and an impact force at this time is measured. Then, the impact absorption rate (%) of the test piece 2 can be measured by calculating the following equation (1).

$$\text{Impact absorption rate } (\%) = \frac{[(\text{Impact force of only supporting plate} - \text{Impact force when test piece is inserted})]}{\text{Impact force of only supporting plate}} \times 100 \quad (1)$$

Next, a method of measuring the displacement of the test piece 2 when the hammer 24 is brought into collision with the supporting plate 28 will be described.

The impact force applied to the test piece 2 is sensed by the above-described method by the force sensor 5 when the hammer 24 is brought into collision with the supporting plate 28. A signal from the force sensor 5 is inputted to the synchronizing section 35. On the other hand, the displacement of the test piece 2 at this time is taken by the high-speed camera 6 and an image pickup signal from the high-speed camera 6 is inputted to the synchronizing section 35 via the first control section 32. Here, the synchronization between a signal from the force sensor 5 and a signal from the high-speed camera 6 is achieved by the synchronizing section 35 in the following manner: as shown in FIG. 4, when the hammer 24 passes by the speed sensor 34 disposed just before the holding device 3, a signal is sent out by the speed meter 33, thereby being inputted to the first control section 32 and at the same time a synchronizing signal is inputted to the synchronizing section 35 via the first control section 32; then, at the timing of the signal from the speed meter 33, the high-speed camera 6 starts picking up an image and the synchronizing section 35 starts sending a signal of the force sensor 5; with this, the picking-up of the image by the high-speed camera 6 and the measuring of the impact force by the force sensor 5 are started at the same time and hence the displacement of the test piece 2 at each measuring time can be measured in synchronization with the impact force applied to the test piece 2.

(Outputting Step)

The signal from the force sensor 5 and the image pickup signal from the high-speed camera 6, which are synchronized with each other by the synchronizing section 35, are inputted to the second control section 30. In this second control section 30, the signal from the force sensor 5 is converted to an impact force and the image pickup signal from the high-speed camera 6 is subjected to an image processing, thereby being converted to a displacement. Here, the conversion of the image pickup signal from the high-speed camera 6 to the displacement by the image processing is performed by converting the path of a mark put on the end surface of the test piece 2 or the supporting plate 28 into numerals. Further, the second control section 30 acquires data of the impact force and the displacement at each measuring time and then divides the impact force by the area of such surface of the test piece 2 that abuts against the supporting plate 28 and divides the displacement by the thickness of the test piece when load is not applied to the test piece 2, thereby being able to output an impact stress-strain characteristic curve. For example, when the second control section 30 is constructed of a personal computer or the like having a liquid crystal display screen, the impact stress-strain characteristic curve can be displayed on the liquid crystal display screen.

In this manner, even if the test piece 2 is made of a foaming material, a viscoelastic material, or a combination of these materials, that is, made of an impact absorbing material that damps or absorbs an impact force when the impact force is applied to the test piece 2, the impact test apparatus 1 can output an impact stress-strain characteristic curve when the impact force is applied to the test piece 2. Moreover, the impact test apparatus 1 can output also the impact absorption rate of the test piece 2 at the same time.

Here, one example of an impact test will be described which was conducted on a test piece 2, which was formed of a foaming material made of polypropylene and was set in the impact test apparatus 1 of the above construction.

This test piece 2 was cut out of an impact absorbing material formed of a foaming material so as to have a size of 20 mm×20 mm×1 mm and then was held by the holding device 3 via the supporting plate 28 made of acrylic resin having a size of 90 mm×80 mm×3 mm. At this time, the pressing member 12 was slightly pressed in from the base point to hold the test piece 2 in a state where the test piece 2 was compressed by 30% in the direction of thickness. Then, the hammer 24 was set in a state where the hammer 24 was swung up at 45° with respect to the support column 20 and then the hammer 24 was separated from the arm 21, thereby being brought into collision with the supporting plate 28. At this time, the displacement image of the test piece 2 was picked up on a needed basis by the high-speed camera 6 (for example, FASTCAM manufactured by Photron). This impact test was conducted under environment of room temperature of 20° C. and humidity of 60%.

Figure 5:
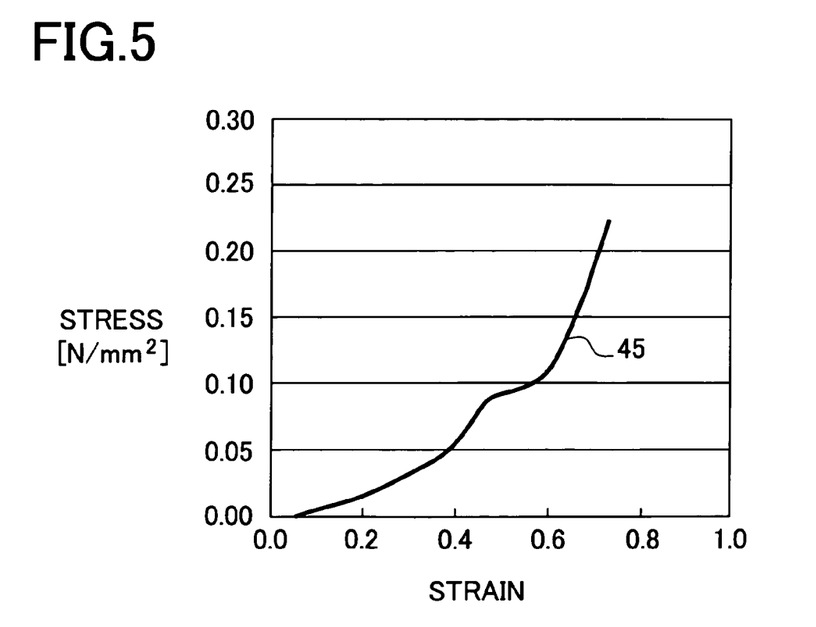
FIG. 5 is a graph showing one example of an impact stress-strain characteristic curve obtained by the impact test apparatus in the first embodiment.

An impact stress-strain characteristic curve 45 obtained under the test conditions described above is shown in FIG. 5. As shown in FIG. 5, even if the test piece 2 was made of the impact absorbing material such as a foaming material of polypropylene, the impact stress-strain characteristic curve 45 could be obtained.

Figure 6:
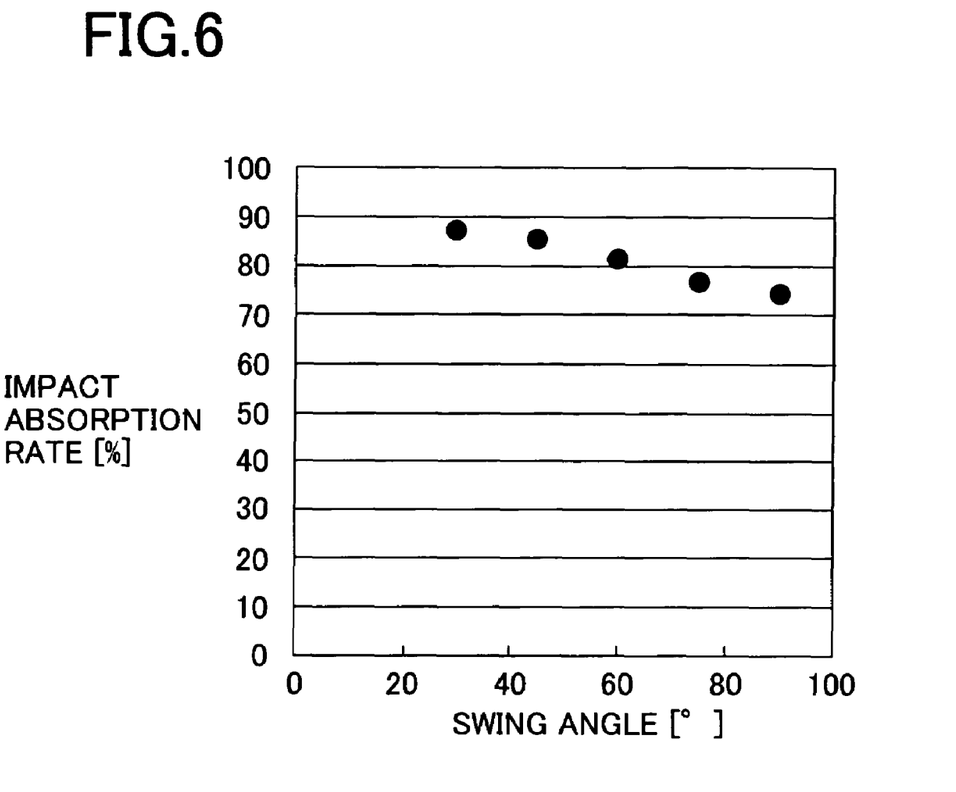
FIG. 6 is a graph showing one example of an impact absorption rate with respect to a swing angle of a hammer obtained by the impact test apparatus in the first embodiment.

Further, the test piece 2 was held in a state where it was compressed by 30% in the direction of thickness and was set in a state where the hammer 24 was swung up to angles of 30°, 45°, 60°, 75°, and 90° and then the hammer 24 was separated from the arm 21, thereby being brought into collision with the supporting plate 28. The impact absorption rates of the test piece 2, which were obtained by the above equation (1), are shown in FIG. 6. As shown in FIG. 6, even if the test piece 2 was made of the impact absorbing material such as a foaming material of polypropylene, the impact absorption rates of the test piece 2 with respect to the respective angles to which the hammer 24 was swung up could be obtained.

Embodiment 2

Next, the schematic construction of an impact test apparatus in a second embodiment will be described with reference to FIGS. 7 to 9. Here, in the following description, the same reference symbols as in the construction or the like of the impact test apparatus 1 in the first embodiment shown in FIGS. 1 to 4 denote the same or equivalent parts as in the construction or the like of the impact test apparatus 1 in the first embodiment.

The schematic construction and control construction of an impact test apparatus in the second embodiment are nearly equal to those of the impact test apparatus 1 in the first embodiment.

Figure 7:
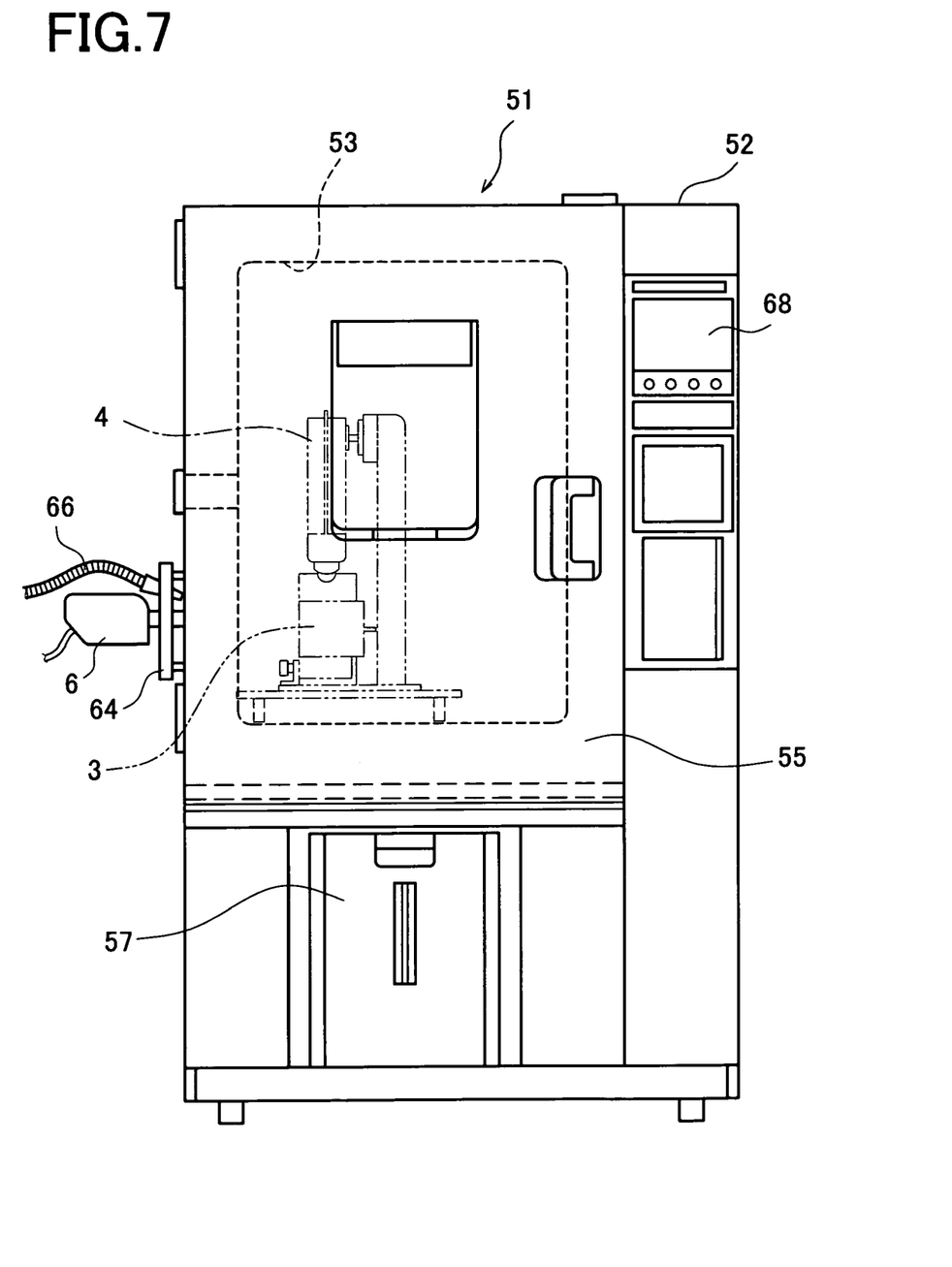
FIG. 7 is a front view showing a schematic construction of an impact test apparatus in a second embodiment.
Figure 8:
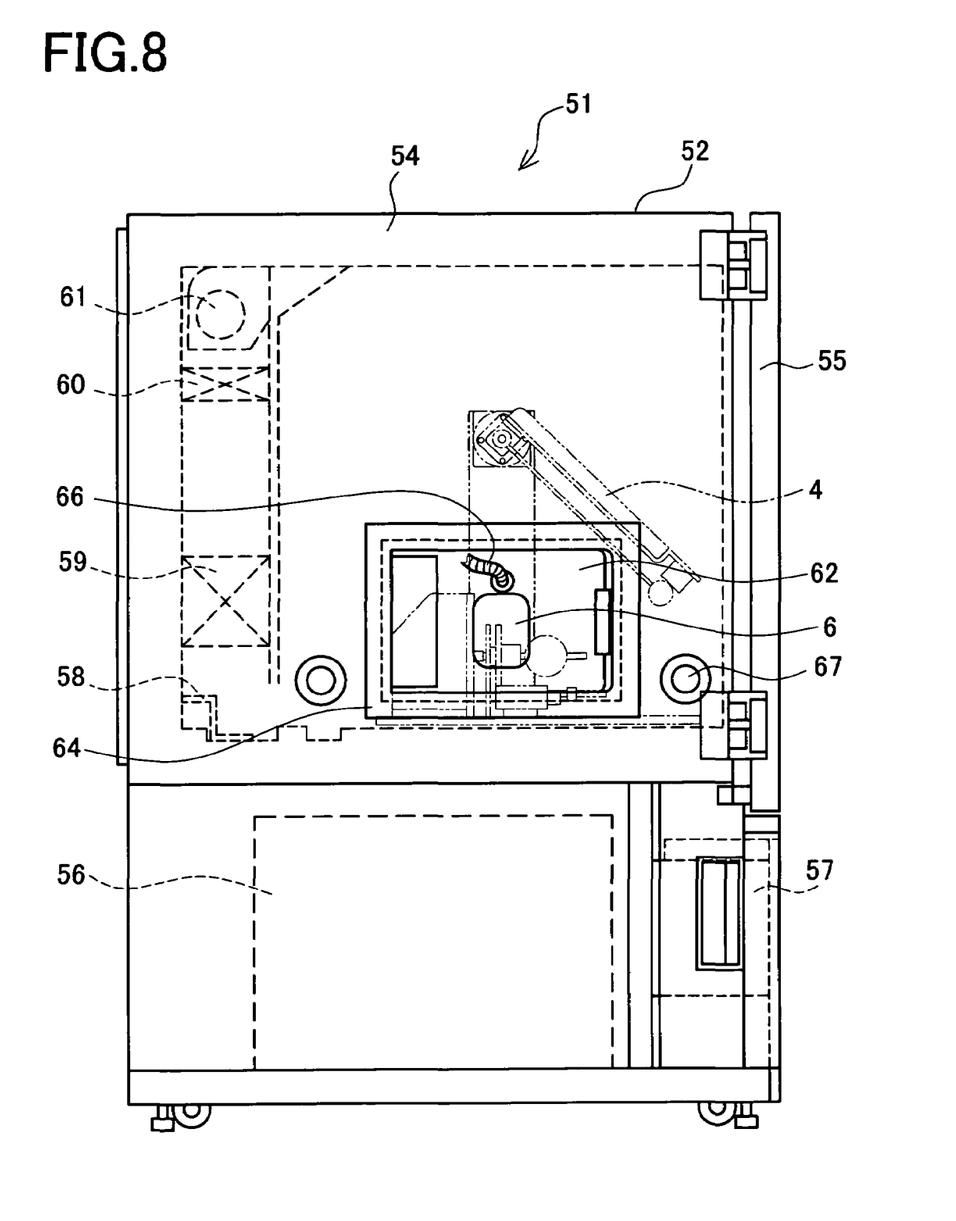
FIG. 8 is a left side view showing the schematic construction of the impact test apparatus in the second embodiment.
Figure 9:
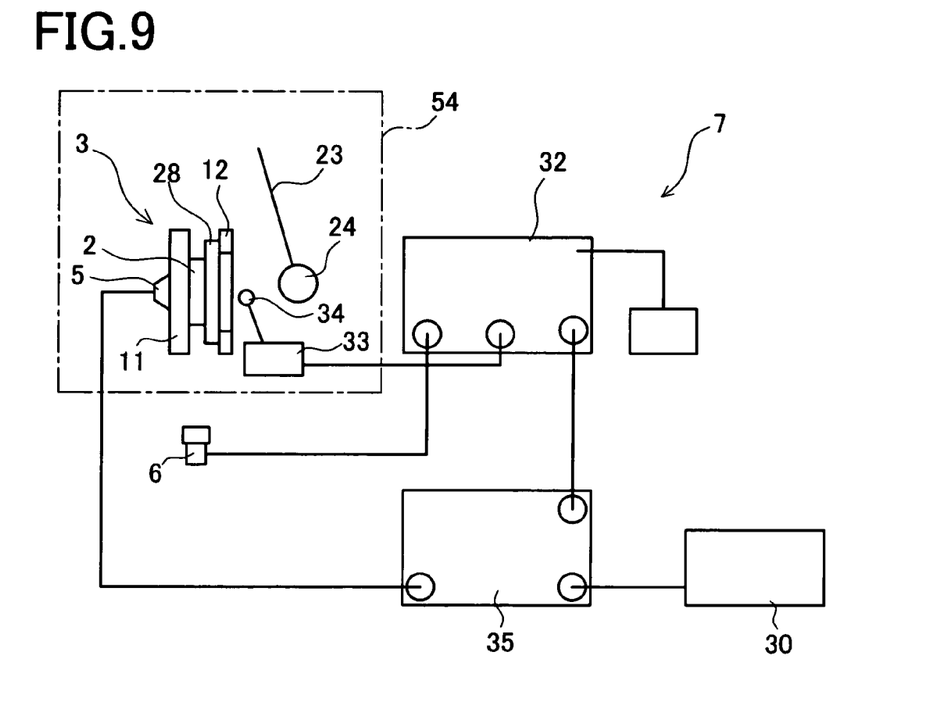
FIG. 9 shows the schematic construction of an output device that detects the impact force and displacement of a test piece and outputs an impact stress-strain characteristic information in the impact test apparatus in the second embodiment.

However, as shown in FIGS. 7 to 9, an impact test apparatus 51 in the second embodiment is different from the construction of the impact test apparatus 1 in the first embodiment in that the holding device 3 having the force sensor 5 fixed thereto and the impact applying device 4, which construct the impact test apparatus 1 in the first embodiment, are disposed in a thermal insulating housing 54 of a thermo-hygrostat 52 as a temperature keeping device and humidity keeping device.

As shown in FIG. 7 and FIG. 8, the thermo-hygrostat 52 is constructed of: the thermal insulating housing 54 having a square opening 53 on the front surface; a thermal insulating door 55 turnably supported by the end portion on one side of the opening 53 so that it may pivot and close the opening 53, and mounted so that it can be freely opened or closed; and a refrigerator unit 56 disposed under the thermal insulating housing 54. Further, in the back of the thermal insulating housing 54 are disposed: a humidifier 58 having water supplied from a water supply tank 57 disposed on the front side of the refrigerator unit 56; a cooling-dehumidifying device 59 disposed above the humidifier 58 and cooled by the refrigerator unit 56; a heater 60 disposed above the cooling dehumidifying device 59; and a blower 61 disposed above the heater 60. Moreover, a humidity sensor and a temperature sensor (both not shown) are disposed near the blowoff port of the blower 61.

Further, an observation window 62 is formed in the lower central portion of the side wall of the thermal insulating housing 54 and hence the displacement of the test piece 2 held by the holding device 3 disposed in the thermal insulating housing 54 can be observed through the observation window 62. Still further, a protecting plate 64, which is formed of a clear acrylic plate or the like and has a vertically elongated through hole formed nearly in the center and is formed nearly in a square, is provided outside the observation window 62. The high-speed camera 6 and an illuminating device 66 are disposed outside the protecting plate 64. With this, the displacement of the test piece 2 held by the holding device 3 can be observed.

Further, a wire pull-out port 67 used for pulling out wires from the electric magnet 25 of the impact applying device 4, the speed meter 33, and the force sensor 5, which are disposed in the thermal insulating housing 54, is provided on the side of the observation window 62.

Still further, an operating part 68, which is provided with a control circuit (not shown) for driving and controlling the refrigerator unit 56, the humidifier 58, the cooling dehumidifying device 59, the heater 60, and the blower 61, is provided on the right side of the thermal insulating door 55 and can set temperature and humidity in the thermal insulating housing 54 at a predetermined temperature and at a predetermined humidity. Here, in the thermo-hygrostat 52, temperature in the thermal insulating housing 54 can be set at an arbitrary temperature within a range of from −40° C. to 100° C. and humidity in the thermal insulating housing 54 can be set at an arbitrary humidity within a range of from 0% to 100%.

Still further, as shown in FIG. 9, the speed sensor 34 provided before the test piece 2 and the speed meter 33 connected to the speed sensor 34 are disposed in the thermal insulating housing 54.

Still further, as shown in FIG. 9, the output device 7 for outputting an impact stress-strain characteristic curve is disposed outside the thermal insulating housing 54 and is constructed of the first control section 32 for outputting a displacement detecting signal (image signal) from the high-speed camera 6 serving as the displacement detecting device; the synchronizing section for synchronizing a signal from the force sensor 5 serving as the impact force sensing device with a displacement detecting signal (image signal) from the first control section 32; and the second control section 30 that analyzes an image of the displacement detecting signal (image signal) from the first control section 32, divides a displacement by the thickness of the test piece 2 when load is not applied thereto to calculate a strain, analyzes a signal from the force sensor 5 synchronized by the synchronizing section 35 and calculates an impact force, divides the impact force by the area of such surface of the test piece 2 that abuts against the supporting plate 28 to calculate an impact stress, and outputs an impact stress-strain characteristic curve. Here, the synchronization between the signal from the force sensor 5 and the displacement detecting signal (image signal) from the first control section 32 is achieved by the simultaneous detection of the respective signals by the first control section 32 and the synchronizing section 35 at the timing of a signal from the speed meter 33 outputted when the hammer 24 passes before the speed sensor 34 disposed before the test piece 2.

Next, an impact test method using the impact test apparatus 51 constructed in the manner described above will be described.

(Holding Step)

First, the test piece 2 is not inserted between the fixing jig 11 and the pressing member 12 of the holding device 3 disposed in the thermal insulating housing 54 but only the supporting plate 28 made of acrylic resin is inserted. Then, the base 13 is slid to the fixing jig 11 side by the lever 14, thereby being brought into nearly close contact with the supporting plate 28 and then being temporarily fixed there. Next, the base 13 is finely adjusted by the pressing pressure adjusting unit 16 to put the fixing jig 11 into close contact with the supporting plate 28. At this time, a memory provided in the pressing pressure adjusting unit 16 is reset and the position of the pressing member 12 is made a base point.

Next, the thickness of the test piece 2 is previously measured in the room. Then, the pressing pressure adjusting unit 16 is adjusted to move the pressing member 12 from the base point by the thickness of the test piece 2 to set the test piece 2 between the fixing jig 11 and the supporting plate 28. At this time, in the case of setting the test piece 2 made of an impact absorbing material, which is made of a foaming material, a viscoelastic material, or a combination of these materials and damps and absorbs an impact when the impact is applied to the test piece 2, in the holding device 3, a pressing pressure is adjusted while checking the gage of the pressing pressure adjusting unit 16 and considering the thickness of the test piece 2. In this manner, the test piece 2 can be fixed at a compression rate close to a compression rate in the actual state of placement of a product. Further, when an adhesive agent or the like is applied to a portion or the whole of one surface of the test piece 2, the test piece 2 can be placed on the fixing jig 11 and hence can be fixed to the fixing jig 11 with reliability. Then, after the test piece 2 is set, the switch of the electric magnet 25 provided at one end of the arm 21 is turned on and the hammer 24 is fixed to and held by the arm 21. Then, the arm 21 is swung up to an arbitrary predetermined angle and is fixed there.

(Temperature Keeping Step and Humidity Keeping Step)

Then, after the arm 21 is set at the arbitrary predetermined angle, the thermal insulating door 55 is closed and then the set temperature and the set humidity of the thermo-hygrostat 52 are set at a predetermined temperature and at a predetermined humidity by the operating part 68 and is operated for a predetermined time (for example, approximately from 30 minutes to two hours). With this, the temperature of the test piece 2 can be increased to the set temperature with reliability and the test piece 2 can be held in the atmosphere of the set humidity.

(Impact Applying Step)

Thereafter, the switch of the electric magnet 25 is turned off to bring the hammer 24 into collision with the supporting plate 28 held by the holding device 3 (see FIG. 9).

(Detecting Step)

Moreover, an impact force at this time is measured by the force sensor 5.

Here, the fixing jig 11 is put into close contact with the supporting plate 28 before the test piece 2 is inserted between them and then the hammer 24 is similarly brought into collision with the supporting plate 28 and an impact force at this time is measured. Then, the impact absorption rate (%) of the test piece 2 can be measured in the atmosphere of the respective set temperatures and humidities by calculating the above-described equation (1).

Next, a method of measuring the displacement of the test piece 2 when the hammer 24 is brought into collision with the supporting plate 28 will be described.

The impact force applied to the test piece 2 is sensed by the above-described method by the force sensor 5 when the hammer 24 is brought into collision with the supporting plate 28. A signal from the force sensor 5 is inputted to the synchronizing section 35. On the other hand, the displacement of the test piece 2 at this time is picked up through the observation window 62 by the high-speed camera 6 and an image pickup signal from the high-speed camera 6 is inputted to the synchronizing section 35 via the first control section 32. Here, the synchronization between the signal from the force sensor 5 and the signal from the high-speed camera 6 is achieved by the synchronizing section 35 in the following manner: as shown in FIG. 9, when the hammer 24 passes by the speed sensor 34 disposed just before the holding device 3, a signal is sent out by the speed meter 33, thereby being inputted to the first control section 32 and at the same time a synchronizing signal is inputted to the synchronizing section 35 via the first control section 32; then, at the timing of the signal from the speed meter 33, the high-speed camera 6 starts taking an image and the synchronizing section 35 starts sending the signal of the force sensor 5; with this, the taking of the image by the high-speed camera 6 and the measuring of the impact force by the force sensor 5 are started at the same time and hence the displacement of the test piece 2 at each measuring time can be measured in synchronization with the impact force applied to the test piece 2 in the atmosphere of the set temperature and the set humidity.

(Outputting Step)

Then, the signal from the force sensor 5 and the image pickup signal from the high-speed camera 6, which are synchronized with each other by the synchronizing section 35, are inputted to the second control section 30. In this second control section 30, the signal from the force sensor 5 is converted to an impact force and the image pickup signal from the high-speed camera 6 is subjected to an image processing, thereby being converted to a displacement. Here, the conversion of the image pickup signal from the high-speed camera 6 to the displacement by the image processing is performed by converting the path of a mark put on the end surface of the test piece 2 or the supporting plate 28 into numerals.

Further, the second control section 30 acquires data of the impact force and the displacement at each measuring time and then divides the impact force by the area of such surface of the test piece 2 that abuts against the supporting plate 28 and divides the displacement by the thickness of the test piece when load is not applied to the test piece 2, thereby being able to output an impact stress-strain characteristic curve in the atmosphere of the set temperature and set humidity. For example, when the second control section 30 is constructed of a personal computer or the like having a liquid crystal display screen, the impact stress-strain characteristic curve in the atmosphere of the set temperature and set humidity can be displayed on the liquid crystal display screen.

In this manner, the impact stress-strain characteristic curve in the atmosphere of the set temperature and set humidity can be outputted. Hence, for example, even if the test piece 2 is made of a foaming material, a viscoelastic material, or a combination of these materials, that is, made of an impact absorbing material that damps or absorbs an impact force when the impact force is applied to the test piece 2, the impact test apparatus 51 can output an impact stress-strain characteristic curve when an impact force is applied to the test piece 2 in the atmosphere of the arbitrary set temperature and set humidity. Moreover, at the same time, the impact test apparatus 51 can output also the impact absorption rate of the test piece 2 in the atmosphere of the arbitrary set temperature and set humidity.

Here, one example of an impact test will be described which was conducted on a test piece 2, which was formed of a foaming material made of polypropylene and was set in the impact test apparatus 51 of the above construction, at set temperatures of −20° C., +20° C., and +60° C. and at a set humidity of 60%.

This test piece 2 was cut out of an impact absorbing material formed of a foaming material of polypropylene so as to have a size of 20 mm×20 mm×1 mm and then was held by the holding device 3 via the supporting plate 28 made of acrylic resin and having a size of 90 mm×80 mm×3 mm. At this time, the pressing member 12 was slightly pressed in from the base point to hold the test piece 2 in a state where the test piece 2 was compressed by 30% in the direction of thickness.

Then, the hammer 24 was set in a state where the hammer 24 was swung up at 45° with respect to the support column 20 and then was left at the set temperatures of −20° C., +20° C., and +60° C. and at the set humidity of 60% for approximately one hour. Then, the hammer 24 was separated from the arm 21, thereby being brought into collision with the supporting plate 28. At this time, the displacement image of the test piece 2 was picked up on a needed basis by the high-speed camera 6 (for example, FASTCAM manufactured by Photron).

Figure 10:
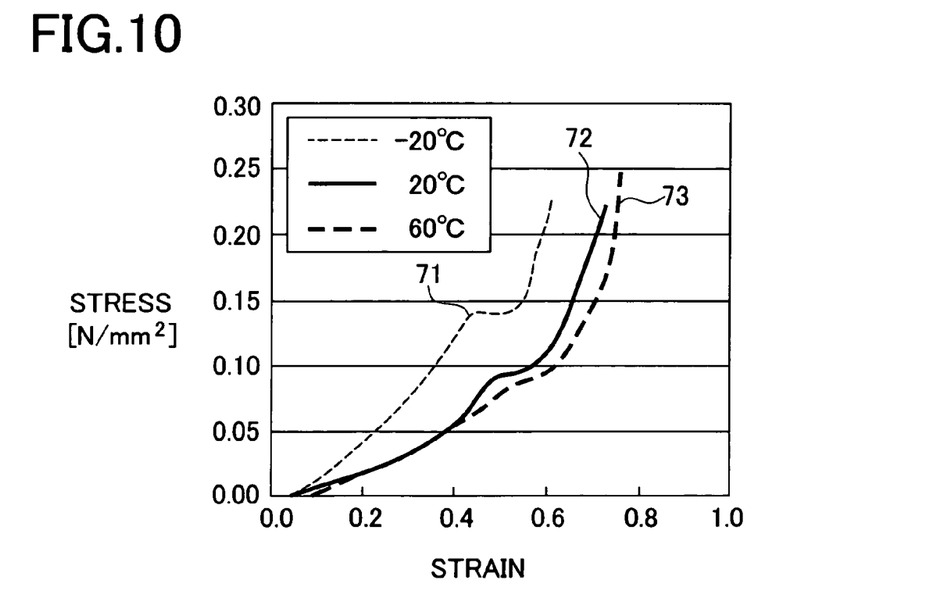
FIG. 10 is a graph showing respective impact stress-strain characteristic curves obtained by the impact test apparatus in the second embodiment at set temperatures of −20° C., +20° C., and +60° C. and at a set humidity of 60%.

Impact stress-strain characteristic curves 71, 72, and 73 obtained under the test conditions described above at the set temperatures of −20° C., +20° C., and +60° C. and at the set humidity of 60% are shown in FIG. 10. As shown in FIG. 10, even if the test piece 2 was made of the impact absorbing material such as a foaming material of polypropylene, the impact stress-strain characteristic curves 71, 72, and 73 at the set temperatures of −20° C., +20° C., and +60° C. and at the set humidity of 60% could be obtained.

Here, needless to say, the present invention is not limited to the above-described first and second embodiments but may be variously improved and modified without departing from the scope of the present invention, which is set forth in the appended claims. For example, the invention may be modified as follows.

Embodiment 3

Figure 11:
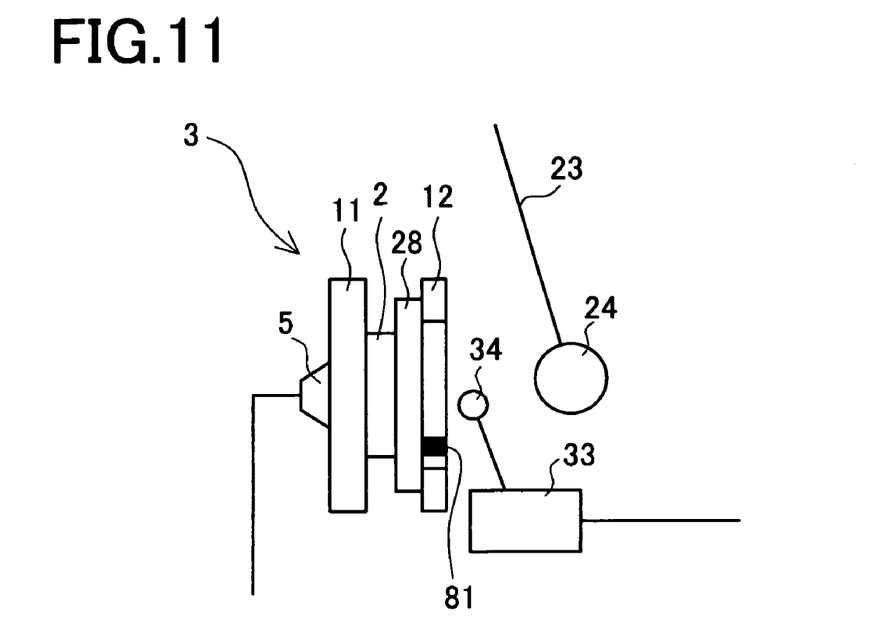
FIG. 11 is a partial enlarged view showing a state where an acceleration sensor is fixed to the supporting plate of a holding device of the impact test apparatus in another embodiment.

As shown in FIG. 11, in place of measuring the displacement of the test piece 2 by the use of the above-described high-speed camera 6, for example, an acceleration sensor 81 is fixed in a position close to a portion where the hammer 24 is brought into collision with the supporting plate 28 and an acceleration when the hammer 24 is brought into collision with the supporting plate 28 is integrated twice. With this, the displacement of the test piece 2 can be also found.

Embodiment 4

Figure 12:
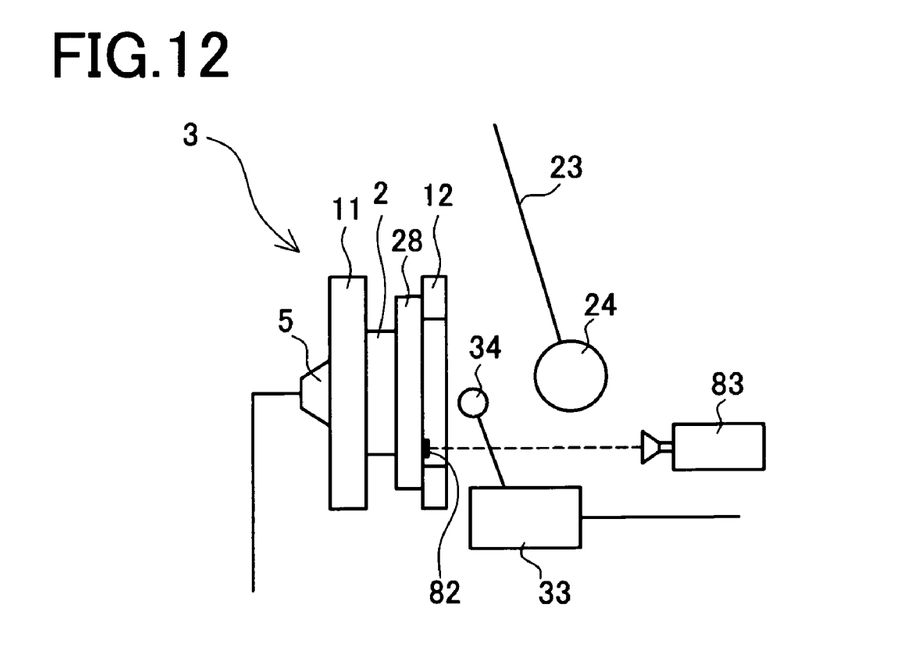
FIG. 12 illustrates a method of measuring the displacement of a metal foil placed on the supporting plate of a holding device of the impact test apparatus in another embodiment by a laser Doppler vibrometer.

As shown in FIG. 12, in place of measuring the displacement of the test piece 2 by the use of the above-described high-speed camera 6, a metal foil 82 is placed on the supporting plate 28 and a laser is applied to the metal foil 82 from a laser Doppler vibrometer to vibrate the metal foil. With this, the displacement of the test piece 2 can be also measured by the vibration of the metal foil 82.

Embodiment 5

Further, in the above first and second embodiments, cases where the test piece 2 is held via the supporting plate 28 have been described as examples. However, for example, an impact force is uniformly applied to the whole surface of the test piece 2 made of impact absorbing material of a foaming material, a viscoelastic material, or a combination of these materials, by using a block-shaped part as the hammer 24, without using the supporting plate 28. With this, the impact stress-strain characteristic curve and the impact absorption rate of the test piece 2 can be also obtained.

What is claimed is:

1. An impact test apparatus comprising:
   a holding device for holding a thin test piece made of an impact absorbing material at an arbitrary compression rate in a thickness direction;
   an impact applying device for applying an impact force to the test piece held by the holding device;
   an impact force sensing device for sensing the impact force applied to the test piece by the impact applying device;
   a displacement detecting device for detecting a displacement of the test piece when the impact force sensing device senses the impact force; and
   an output device for outputting impact stress-strain characteristic information expressing a relationship between an impact stress and a strain corresponding to the impact stress of the test piece on the basis of the impact force sensed by the impact force sensing device and the displacement detected by the displacement detecting device;

wherein the holding device includes:
  a plate-shaped fixing jig which is vertically fixed to a table and movable into close contact with one side of the test piece:
  a supporting plate which is movable into close contact with the other side of the test piece fixed with the fixing jig;
  a pressing member centrally formed with an opening and placed to be slidable toward the fixing jig so that the pressing member is fixed to the table in contact with a surface of the supporting plate opposite a surface placed in contact with the test piece. thereby pressing the supporting plate against the test piece; and
  a pressing pressure adjusting unit for adjusting pressing pressure of the pressing member with respect to the supporting plate to arbitrarily set the compression rate in the thickness direction;

and wherein:
the impact applying device is movable into the opening of the pressing member to apply an impact force to the supporting plate,
the impact force sensing device has a force sensor for detecting the impact force, the force sensor being disposed on a surface of the fixing jig opposite a surface to be brought in close contact with the test piece, and
the displacement detecting device detects a displacement of the supporting plate in a direction toward the fixing jig as the displacement of the test piece in the thickness direction.

2. The impact test apparatus according to claim 1, further comprising a temperature keeping device for keeping the test piece held by the holding device at a predetermined temperature, wherein the predetermined temperature can be changed.

3. The impact test apparatus according to claim 2, further comprising a humidity keeping device for keeping the test piece held by the holding device in an atmosphere of a predetermined humidity, wherein the predetermined humidity can be changed.

4. The impact test apparatus according to claim 1, wherein the impact applying device includes:
  a swing type hammer whose one end is turnably attached; and
  a hammer holding device for holding the hammer, lifting the hammer to a predetermined angle, and swinging down the hammer held by the hammer holding device to apply the impact force to the test piece.

5. The impact test apparatus according to claim 1, wherein the displacement detecting device includes a high-speed camera and detects the displacement of the supporting plate in the direction toward the fixing jig by the high-speed camera.

6. An impact test method comprising the steps of:
  holding a thin test piece made of an impact absorbing material at an arbitrary compression rate in a thickness direction by a holding device;
  applying an impact force to the test piece held at the holding step by an impact applying device;
  sensing the impact force applied to the test piece at the impact applying step by an impact force sensing device and detecting a displacement of the test piece when the impact force sensing device senses the impact force by a displacement detecting device; and
  outputting impact stress-strain characteristic information expressing a relationship between an impact stress and a strain corresponding to the impact stress of the test piece on the basis of the impact force and the displacement, which are sensed and detected at the detecting step, by an output device, wherein the holding device includes:
  a plate-shaped fixing jig which is vertically fixed to a table and movable into close contact with one side of the test piece;
  a supporting plate which is movable into close contact with the other side of the test piece fixed with the fixing jig;
  a pressing member centrally formed with an opening and placed to be slidable toward the fixing jig so that the pressing member is fixed to the table in contact with a surface of the supporting plate opposite a surface placed in contact with the test piece, thereby Pressing the supporting plate against the test piece; and
  a pressing pressure adjusting unit for adjusting pressing pressure of the pressing member with respect to the supporting plate to arbitrarily set the compression rate in the thickness direction;

and further comprising:
moving the impact applying device into the opening of the pressing member to apply an impact force to the supporting plate,
detecting the impact force with a force sensor on the impact force sensing device, the force sensor being disposed on a surface of the fixing jig opposite a surface to be brought in close contact with the test piece, and
detecting, with the displacement detecting device, a displacement of the supporting plate in a direction toward the fixing jig as the displacement of the test piece in the thickness direction,
the holding step including sandwiching the test piece between the fixing jig and the supporting plate, bringing the pressing jig in contact with the supporting plate and fixing the pressing jig the rein, and then adjusting a pressing pressure of the Pressing jig with respect to the supporting plate by means of the pressure adjusting unit to arbitrarily set the compression rate of the test piece in the thickness direction.

7. The impact test method according to claim 6, wherein the displacement detecting device includes a high-speed camera and detects the displacement of the supporting plate in the direction toward the fixing jig by the high-speed camera.

8. The impact test method according to claim 6, wherein the holding step includes a temperature keeping step of keeping the held test piece at a predetermined temperature by a temperature keeping device, wherein the predetermined temperature can be changed.

9. The impact test method according to claim 8, wherein the holding step includes a humidity keeping step of keeping the held test piece at a predetermined humidity by a humidity keeping device, wherein the predetermined humidity can be changed.

10. The impact test method according to claim 6, wherein the impact applying device includes:
  a swing type hammer whose one end is turnably attached; and a hammer holding device for holding the hammer, lifting the hammer to a predetermined angle, and swinging down the hammer to apply the impact force to the test piece.

11. An impact test method comprising the steps of:

applying a first impact force by an impact applying device in a state where a test piece is not set in a holding device;

sensing the first impact force at the first impact applying step by an impact force sensing device;

holding the thin test piece made of an impact absorbing material at an arbitrary compression rate in a thickness direction by the holding device;

applying a second impact force to the test piece held at the holding step by the impact applying device;

sensing the second impact force applied to the test piece at the second impact applying step by the impact force sensing device; and outputting an impact absorption rate of the test piece by dividing a differential impact force, which is found by subtracting the second impact force sensed at the second sensing step from the first impact force sensed at the first sensing step, by the first impact force sensed at the first sensing step to find an impact absorption rate, wherein the holding device includes:

a plate-shaped fixing jig which is vertically fixed to a table and movable into close contact with one side of the test piece;

a supporting plate which is movable into close contact with the other side of the test piece fixed with the fixing jig;

a pressing member centrally formed with an opening and placed to be slidable toward the fixing jig so that the pressing member is fixed to the table in contact with a surface of the supporting plate opposite a surface placed in contact with the test piece, thereby pressing the supporting plate against the test piece; and a pressing pressure adjusting unit for adjusting pressing pressure of the pressing member with respect to the supporting plate to arbitrarily set the compression rate in the thickness direction;

and further comprising:

moving the impact applying device into the opening of the pressing member to apply an impact force to the supporting plate, detecting the second impact force with a force sensor on the impact force sensing unit, the force sensor being disposed on a surface of the fixing jig opposite a surface to be brought in close contact with the test piece; and detecting, with the displacement detecting device, a displacement of the supporting plate in a direction toward the fixing jig as the displacement of the test piece in the thickness direction, the holding step including sandwiching the test piece between the fixing jig and the supporting plate, bringing the pressing jig in contact with the supporting plate and fixing the pressing jig therein, and then adjusting a pressing pressure of the pressing jig with respect to the supporting plate by means of the pressure adjusting unit to arbitrarily set the compression rate of the test piece in the thickness direction.

12. The impact test method according to claim 11, wherein the holding step includes a temperature keeping step of keeping the held test piece at a predetermined temperature by a temperature keeping device, wherein the predetermined temperature can be changed.

13. The impact test method according to claim 12, wherein the holding step includes a humidity keeping step of keeping the held test piece at a predetermined humidity by a humidity keeping device, wherein the predetermined humidity can be changed.

14. The impact test method according to claim 11, wherein the impact applying device includes:

a swing type hammer whose one end is turnably attached; and a hammer holding device for holding the hammer, lifting the hammer to a predetermined angle, and swinging down the hammer to apply the impact force to the test piece.

* * * * *

UNITED STATES PATENT AND TRADEMARK OFFICE
CERTIFICATE OF CORRECTION

PATENT NO. : 7,222,515 B2  Page 1 of 1
APPLICATION NO. : 11/143502
DATED : May 29, 2007
INVENTOR(S) : Takezou Hatanaka et al.

It is certified that error appears in the above-identified patent and that said Letters Patent is hereby corrected as shown below:

Please amend the title page as follows:

Item (73), please change "Nitto Denki Corporation" to --Nitto Denko Corporation--.

Signed and Sealed this

Fourteenth Day of August, 2007

JON W. DUDAS
*Director of the United States Patent and Trademark Office*